United States Patent [19]

Urinowski et al.

[11] Patent Number: 5,363,155
[45] Date of Patent: Nov. 8, 1994

[54] EYE EXAMINATION APPARATUS AND ACCESSORY THEREFOR

[76] Inventors: Ehud Urinowski, 6 Ben Tov Street, 43229 Raanana; Dror Nedivi, 41 A.D. Gordon St., 49280 Petah Tikva; Joseph Petel, 83 Levona, Beit Arie, 71947 Doar Na Modiin, all of Israel

[21] Appl. No.: 19,378

[22] Filed: Feb. 18, 1993

[51] Int. Cl.⁵ .................. A61B 3/10; A61B 3/16
[52] U.S. Cl. .................. 351/205; 128/645; 128/646; 128/652
[58] Field of Search .......... 351/205, 214; 128/645, 128/646, 652

[56] References Cited

U.S. PATENT DOCUMENTS

| | | | |
|---|---|---|---|
| 2,622,473 | 12/1952 | Littmann | 351/214 |
| 2,940,357 | 6/1960 | Oswold | 351/214 |
| 3,452,589 | 7/1969 | Hargens, III et al. | 128/645 |
| 3,470,736 | 10/1969 | Bartfay | 128/652 |
| 3,645,609 | 2/1972 | Holmes | 351/205 |
| 3,693,416 | 9/1972 | Dianetti | 128/652 |
| 3,724,263 | 4/1973 | Rose et al. | 128/646 |
| 3,830,562 | 8/1974 | McGrann et al. | 351/214 |
| 4,456,348 | 6/1984 | Schulz et al. | 351/205 |
| 4,523,597 | 6/1985 | Sawa et al. | 128/652 |
| 4,874,236 | 10/1989 | Abraham | 351/205 |
| 4,987,899 | 1/1991 | Brown | 128/654 |

FOREIGN PATENT DOCUMENTS

| | | | |
|---|---|---|---|
| 1292152 | 3/1962 | France | 128/652 |
| 2307733 | 8/1974 | Germany | 128/645 |
| 862920 | 3/1961 | United Kingdom | 128/652 |
| 1360603 | 7/1974 | United Kingdom | 128/652 |

OTHER PUBLICATIONS

"The new Zeiss Applanation Tonometer", *Zeiss-Inform.* 24, Sep. 1979, No. 88, p.29.

*Primary Examiner*—Richard A. Bertsch
*Assistant Examiner*—Howard R. Richman
*Attorney, Agent, or Firm*—Benjamin J. Barish

[57] ABSTRACT

An accessory for use with an eye examination apparatus including an eyepiece, a control lever for controlling the position of the eyepiece, and a tonometer unit located rearwardly of the eyepiece and including a contact element which is adjustable for varying the pressure applied by the contact element against the subject's eye. The accessory includes a remote control unit attachable to the apparatus such that a control member in the remote control unit is in the vicinity of the control lever of the apparatus for controlling the position of its eyepiece, and a coupling between the control member and the tonometer unit such as to permit the operation of the control lever and the control member by one hand of the examiner while the examiner views the subject's eye via the eyepiece.

20 Claims, 6 Drawing Sheets

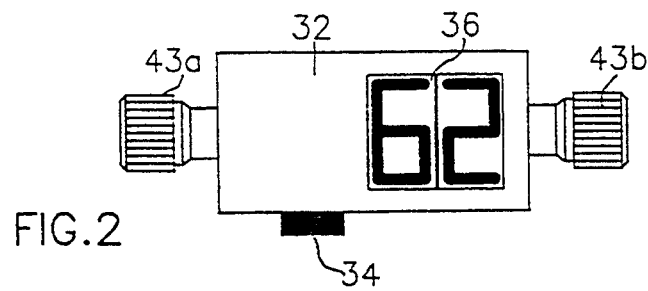
FIG.2
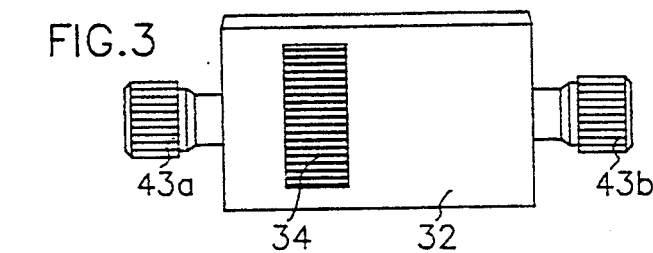
FIG.3
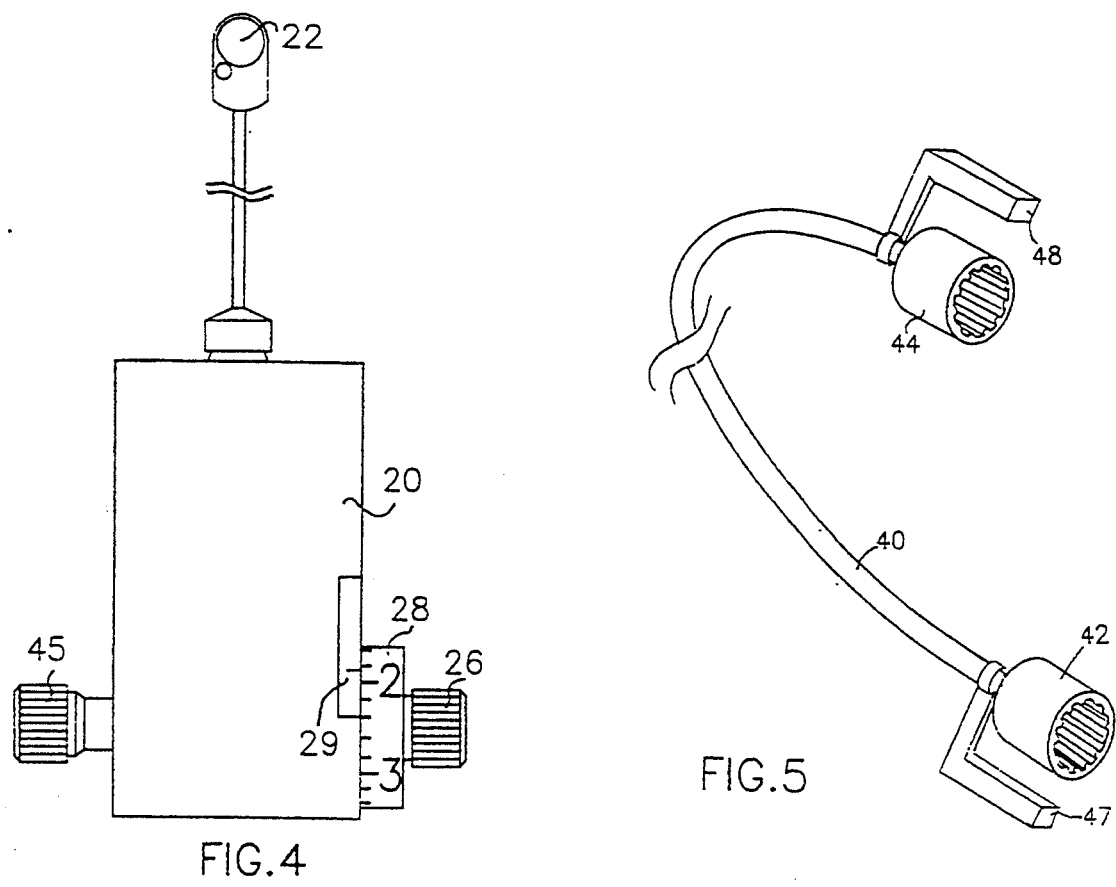
FIG.4
FIG.5

EYE EXAMINATION APPARATUS AND ACCESSORY THEREFOR

FIELD AND BACKGROUND OF THE INVENTION

The present invention relates to an eye examination apparatus including a tonometer for measuring the intraocular pressure of a subject's eye. The invention is especially useful when embodied in an accessory to be attached to existing eye examination apparatus, such as the Goldmann Applanation Tonometer, and is therefore described below with respect to this application.

One of the most common eye examinations carried out by ophthalmologists is an intraocular pressure test. This test is commonly performed on a slit lamp type apparatus equipped with a tonometer unit. The slit lamp comprises a microscope eyepiece carried forwardly of the apparatus to enable an examiner to view a subject's eye located rearwardly of the eyepiece, and a control lever for controlling the position of the eyepiece. The tonometer unit is located rearwardly of the eyepiece and includes a housing, a prism-type contact element to contact the cornea of the subject's eye, and adjusting means including a control knob for varying the pressure applied by the contact element against the subject's eye.

The intraocular pressure test is itself a relatively simple test, but frequently becomes quite complicated, awkward and time-consuming because of the need to adjust both the control lever and the adjusting knob on the tonometer unit at different times during the course of the test. Thus, during one stage, the examiner has to use the fingers of one hand to spread apart the subject's eyelids, and to use the other hand for manipulating both the control lever to control the position of the microscope eyepiece and the control knob on the tonometer unit to adjust the pressure applied to the subject's eye by moving that hand back and forth between the control lever and the control knob.

The existing apparatus makes it very difficult and awkward for the examiner to make the required adjustments in the tonometer and/or in the control lever of the slit lamp without lifting his eyes from the eyepiece, and thereby interrupting visual contact with the subject's eye during these adjustments. Thus, the examiner frequently has to lift his eyes from the eyepiece in order to make an adjustment particularly of the tonometer; but before he resumes viewing through the eyepiece after the adjustment is made, the subject may have moved his eye under examination even slightly. If this should occur, many of the steps of the test, and sometimes the complete test, would have to be repeated. This not only makes the test time-consuming and difficult for the examiner to perform, but also increases the chance of irritating and damaging the subject's eye.

It would therefore be desirable to provide apparatus of the foregoing type which permits the tonometer unit to be adjusted without requiring the examiner to lift his eyes from the eyepiece or his hand from the slit lamp control lever.

OBJECTS AND BRIEF SUMMARY OF THE INVENTION

According to the present invention, there is provided an accessory for use with an eye examination apparatus comprising an eyepiece carried at one side, constituting the forward side, of the apparatus to enable an examiner to view a subject's eye located at the opposite side, constituting the rear side, of the apparatus rearwardly of the eyepiece; a control lever for controlling the position of the eyepiece; and a tonometer unit located rearwardly of the eyepiece and including a housing, a contact element to contact the cornea of the subject's eye, and adjusting means for varying the pressure applied by the contact element against the subject's eye. The accessory comprises a remote control unit having a manual control member; attaching means for attaching the remote control unit to the apparatus; and a coupling between the manual control member and the adjusting means of the tonometer unit. The manual control member of the remote control unit is located sufficiently close to the control lever of the apparatus for controlling the position of the eyepiece such as to permit the operation of both the control lever and the manual control member by the same one hand of the examiner while the examiner views the subject's eye via the eyepiece without lifting the one hand from the control lever or the examiner's eyes from the eyepiece.

Several embodiments of the invention are described below for purposes of example. In some described embodiments, the coupling is a mechanical coupling; whereas in other described embodiments it is an electrical coupling. In some described embodiments, the eyepiece in the eye examination apparatus is carried by an arm adjustably mounted to a base under the control of the control lever, and the attaching means attaches the remote control unit to the arm. In another described embodiment, the remote control attachment is assembled as one unit with the tonometer to enable quick dismantling of both.

The invention is described below as embodied in an accessory for attachment to existing eye-examination apparatus, particularly the slit lamp type apparatus commonly used by ophthalmologists. Such an accessory would thus enable a tonometer unit applied to a slit lamp type apparatus to be adjusted with the same hand as used for adjusting the control lever while the examiner views the results of the adjustment via the eyepiece, thereby greatly facilitating the adjustment of the tonometer and decreasing the time for making the required examination. It will be appreciated, however, that the invention could also be incorporated in the eye examination apparatus as original equipment.

Further features and advantages of the invention will be apparent from the description below.

BRIEF DESCRIPTION OF THE DRAWINGS

The invention is herein described, by way of example only, with reference to the accompanying drawings, wherein:

FIGS. 2 and 3 are top and front views, respectively, of the remote control unit included in the accessory of FIG. 1;

FIG. 4 is a front elevational view illustrating the tonometer unit in the apparatus of FIG. 1;

FIG. 5 illustrates one form of mechanical coupling that may be included in the accessory illustrated in FIG. 1;

DESCRIPTION OF PREFERRED EMBODIMENTS

Figure 1:
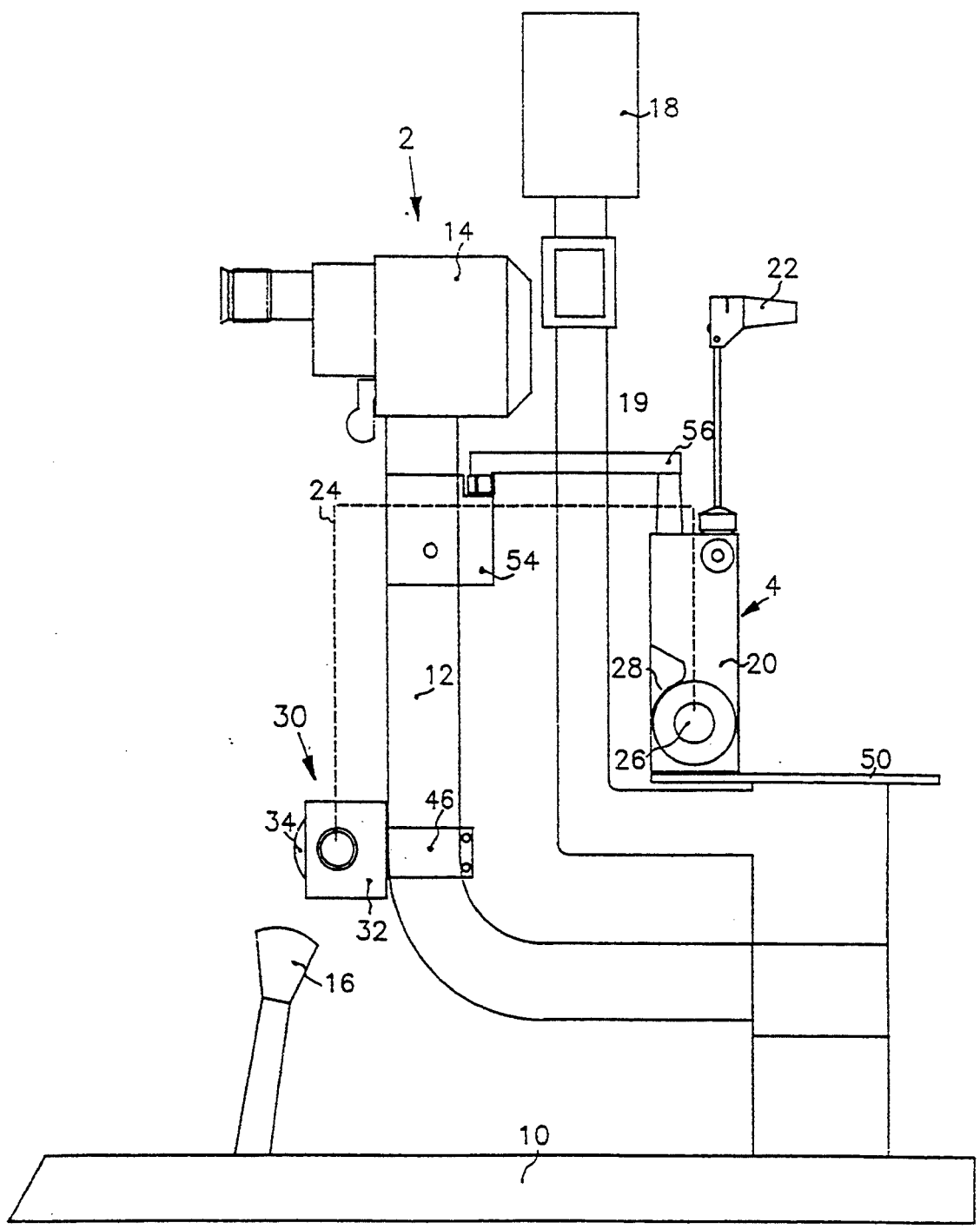
FIG. 1 is a side elevational view illustrating a conventional tonometer apparatus equipped with one form of accessory constructed in accordance with the present invention.

The apparatus illustrated in FIG. 1 is a conventional slit lamp apparatus 2 equipped with a conventional tonometer unit 4 for measuring intraocular pressure of a subject's eye. Slit lamp apparatus 2 includes a base 10 supporting an arm 12 carrying a microscope eyepiece 14 at its upper end forwardly of the apparatus enabling an examiner to view a subject's eye to be located rearwardly of the tonometer unit 4. A control lever 16 controls the position of arm 12, and thereby of the microscope eyepiece 14. A lamp unit 18 is carried at the upper end of a lamp arm 19 between the microscope eyepiece 14 and the tonometer unit 4 for illuminating the eye of the subject.

The tonometer unit 4 includes a housing 20 mounted rearwardly of the slit lamp unit 18 and carries a contact element in the form of a prism 22 adapted to be brought into contact with the cornea of the subject's eye. Contact prism 22 is adjustable, via adjusting means shown schematically at 24, by a rotary knob 26 at the lower end of the housing. Knob 26 may be manually rotated in order to move the contact prism 22 towards or away from the subject's eye to vary the pressure of the prism on the subject's eye during the intraocular pressure examination. An indicia wheel 28, rotated by knob 26 and cooperable with calibration markings 29 (FIG. 4) carried by the housing 4, indicates the amount of rotation of knob 26, and thereby the pressure applied by the prism 22 against the subject's eye.

Since the slit lamp apparatus 2 and the tonometer unit 4 illustrated in FIGS. 1 and 4 are both well known, further details of their construction, operation, and the manner of their use during an examination, are not further described herein except to refer to the above-noted drawbacks in the use of such apparatus, which may not only increase the time and difficulty of the examination, but may also increase the possibility of irritation or damage to the subject's eye.

FIG. 1 illustrates an attachment, generally designated 30, to be used with the illustrated apparatus for permitting the adjustment of the prism contact element 22 of the tonometer 4 in a much more facile, quick, and convenient manner. Briefly, the accessory illustrated in FIG. 1 includes a remote control unit 32 having a manual control member 34 and means for attaching the unit to the apparatus such that the manual control member 34 is in the vicinity of the control lever 16 of the slit lamp apparatus controlling the position of the microscope eyepiece 14. The remote control unit 32 is coupled, by any one of several means to be described more fully below, to the adjusting knob 26 of the tonometer 4, so that the examiner, using one hand, can manipulate both the control lever 16, adjust the slit lamp, and the manual control member 34 of the remote control unit 32 to adjust the contact prism 22, without lifting his or her hand from the control lever 16 or his or her eyes from the microscope eyepiece 14. The examiner can thus continuously view the subject's eye while these adjustments are being made.

The upper face of the remote control unit 32 may be provided with a digital display, as shown at 36 in FIG. 2, calibrated according to the indicia on the indicia wheel 28, for displaying the amount of adjustment of the manual control member 34, and thereby of the measured intraocular pressure.

As described earlier, such an arrangement shortens the time of examination and enables the examiner to continuously view the examined eye during the time of the adjustments. This better enables the examiner to control the adjustments. It also reduces the possibility of irritating or damaging the subject's eye because of poor control of the displacements of the prism contact element 22 of the tonometer, or because of unduly long contact of the prism contact element with the subject's eye.

FIG. 5 illustrates one form of mechanical coupling that may be used for the coupling, schematically indicated at 24 in FIG. 1. As shown in FIG. 4, the mechanical coupling, therein designated 40, includes a socket 42 internally knurled or ribbed, adapted to be received over an externally knurled or ribbed shaft end 43a or 43b, coupled to the manual control member 34 of the remote control unit 32. The opposite end of the mechanical coupling 40 includes a second internally ribbed or knurled socket 44 to be received over a corresponding externally ribbed or knurled shaft end 45 or adjusting knob 26 on the tonometer unit 4. Shaft 45 is coupled, as schematically shown at 24 in FIG. 1, to the adjusting mechanism in the same manner as the manual control knob 26 of the tonometer unit. Thus, the manual control member 34 on the remote control unit 32 may be used for adjusting the amount of pressure applied to the eye by the contact prism 22 of the tonometer unit 4 in the same manner as knob 26 on the tonometer unit itself.

It will thus be seen that the examiner, by using one hand engageable with the control lever 16, also has access (e.g., by the index finger of the same hand) to the manual control member 34 on the remote control unit 32, and therefore may adjust the tonometer without lifting his hand from the control lever 16 and, equally important, without lifting his eyes from the microscope eyepiece 14.

The remote control unit 32 may be secured in any suitable manner to the apparatus of FIG. 1, e.g., by clamping elements 46 carried at the opposite ends of the remote control unit 32 and clamped around arm 12 carrying the microscope eyepiece 14. If desired, the ends of the flexible cable coupling 40 may be secured to the remote control unit 32 and the tonometer 4, respectively, by bracket arms 47 and 48 (FIG. 5).

The tonometer unit 4 may be fixed to the slit lamp apparatus in any suitable manner. For purposes of example, FIG. 1 illustrates the tonometer unit 4 received on a table 50 carried by the lamp arm 19, and secured to a clamping ring 54 on the microscope eyepiece arm 12 by a bracket 56.

In the arrangement illustrated in FIGS. 1-3, the manual control member 34 is in the form of a rotatable knob which is easily rotatable in either direction by the user's index finger while the user still grips the control lever 16; both the tonometer prism 22 and the position of the microscope eyepiece 14 can thus be conveniently adjusted with one hand while the examiner continues to view the subject's eye. Other arrangements may be used for both the manual control member 34, as well as the coupling 36 from it to the tonometer unit 4.

Figure 6:
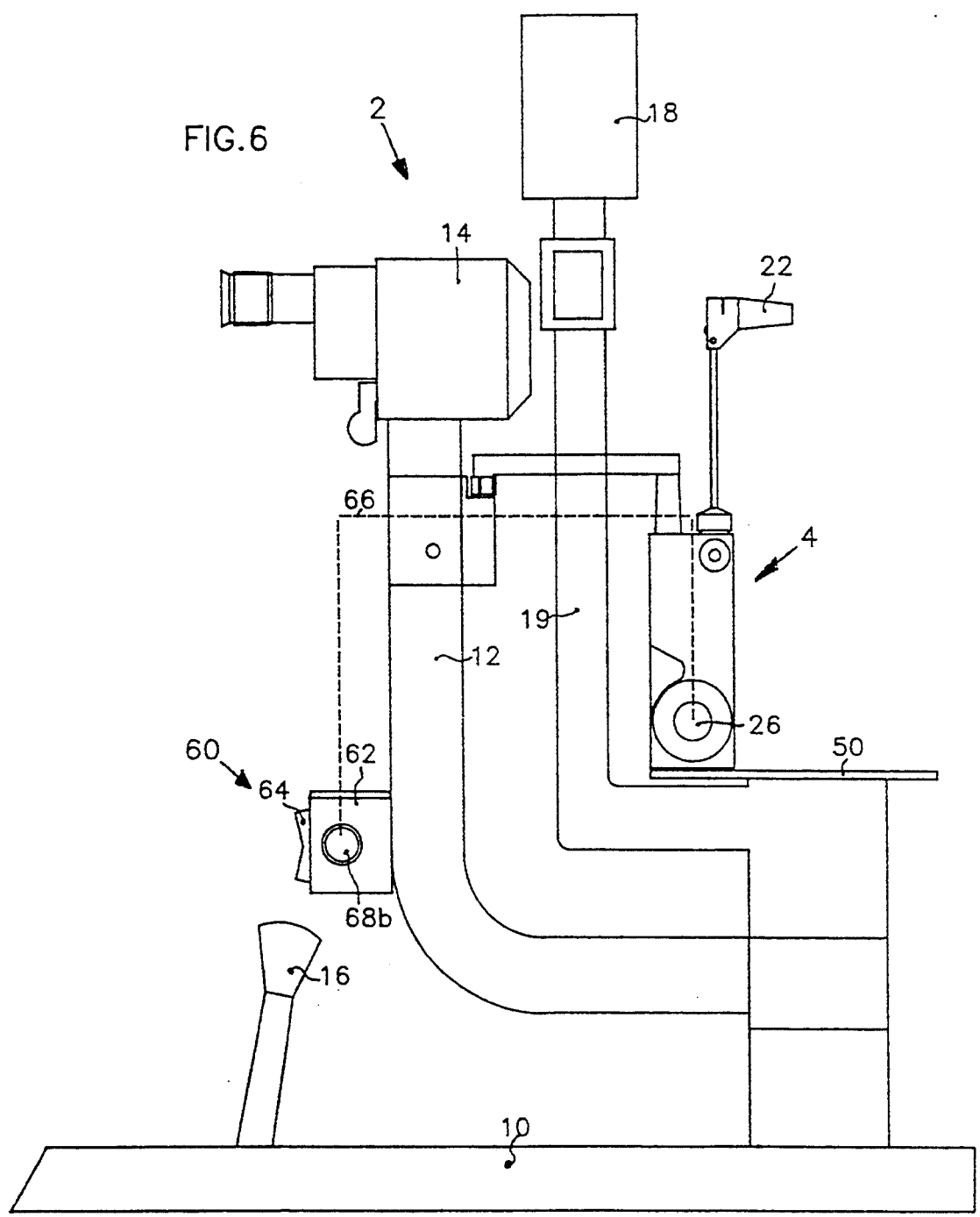
FIGS. 6 and 7 are views corresponding to those of FIGS. 1 and 3 illustrating another form of accessory in accordance with the present invention.
Figure 7:
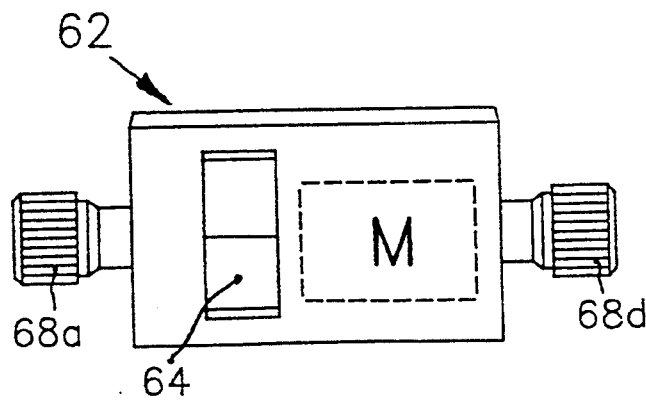

FIGS. 6 and 7 illustrate an accessory, generally designated 60, also including a remote control unit 62 having a manual control member 64, and a flexible-cable type coupling 66 between the remote control unit and the tonometer unit. The tonometer unit in FIG. 6 is of the same construction as tonometer unit 4 in FIGS. 1-4, and therefore its parts are identified by the same reference numbers to facilitate understanding. In the arrangement illustrated in FIGS. 6 and 7, however, the manual control member 64 is in the form of a rocker switch which controls an electrical motor M (FIG. 7) within the remote control unit 62, so that depressing one end of the rocker switch causes the motor M to rotate in one direction, and depressing the opposite end causes it to rotate in the opposite direction. The remote control unit 62 in the accessory of FIGS. 6 and 7 also includes a pair of externally ribbed or knurled shaft ends 68a, 68b, one of which is to be coupled by the same mechanical coupling illustrated in FIG. 5 to the corresponding externally ribbed or knurled shaft end 45 or 26 in the tonometer unit 4.

It will thus be seen that the arrangement illustrated in FIGS. 6 and 7 provides the same advantages as described above with respect to FIGS. 1-5, and operates in the same manner except that, instead of manually rotating the shaft end (68a or 68b) of the remote control unit 62 by a rotatable knob, it is rotated by the electrical motor M within the remote control unit 62 under the control of the rocker switch 64.

Figure 8:
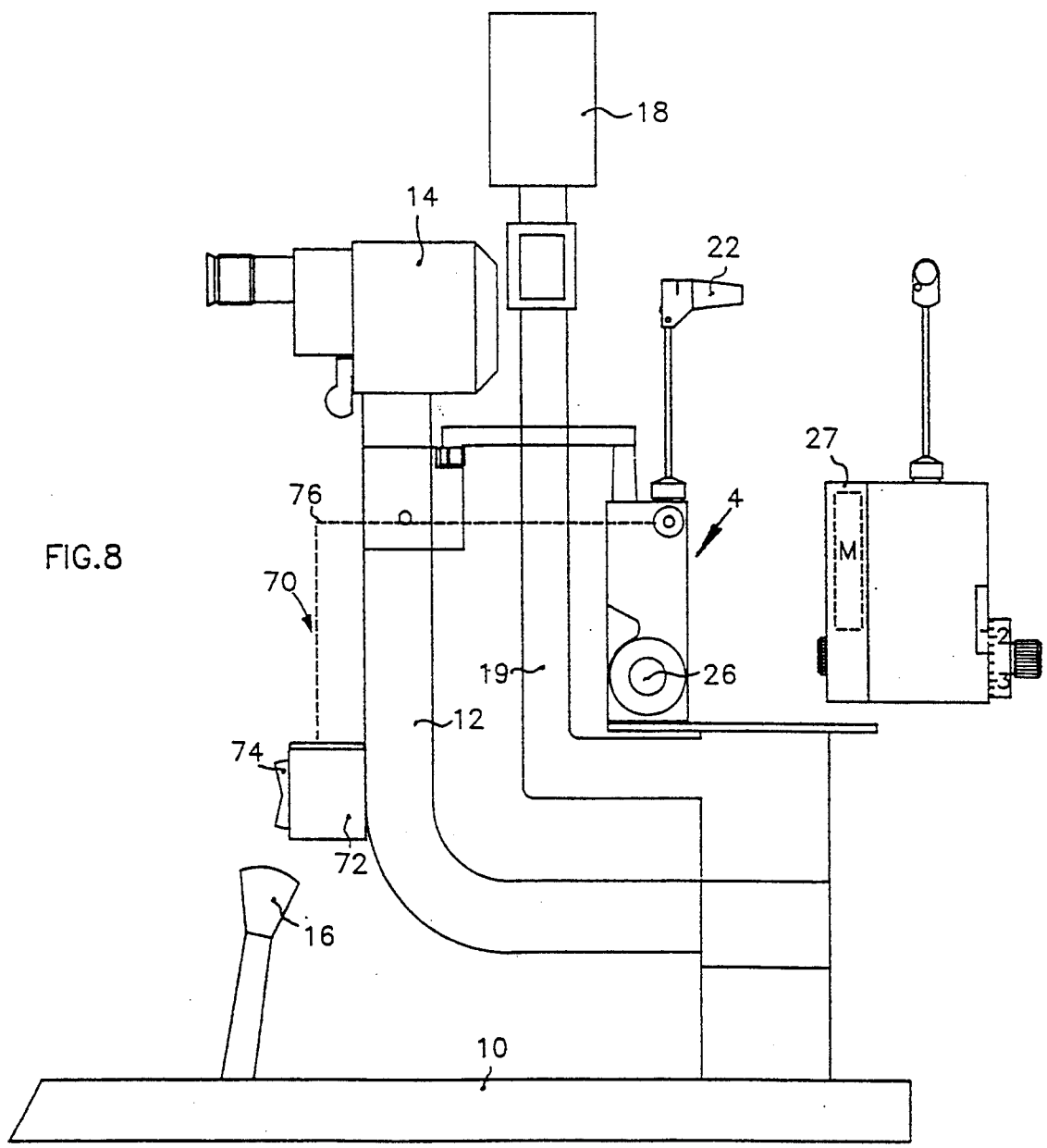
FIGS. 8 and 9 are view corresponding to that of FIG. 1 but illustrating two further forms of accessories in accordance with the present invention.

FIG. 8 illustrates a further variation wherein the accessory, generally designated 70, also includes a remote control unit 72 carrying a rocker switch 74 for controlling an electric motor. In this case, however, the electric motor M is in the slave motor housing 27 attached to the tonometer unit 4 as in FIG. 8a, so that the coupling 76 between the remote control unit 72 and the tonometer unit 4 is an electrical coupling (e.g., a cable), rather than a mechanical coupling. Motor M within the slave motor housing 27 may be a conventional servo motor, e.g., a DC servo motor, which is rotated in one direction when one end of the rocker switch 74 is depressed, and in the opposite direction when the opposite end of the rocker switch is depressed.

Figure 9:
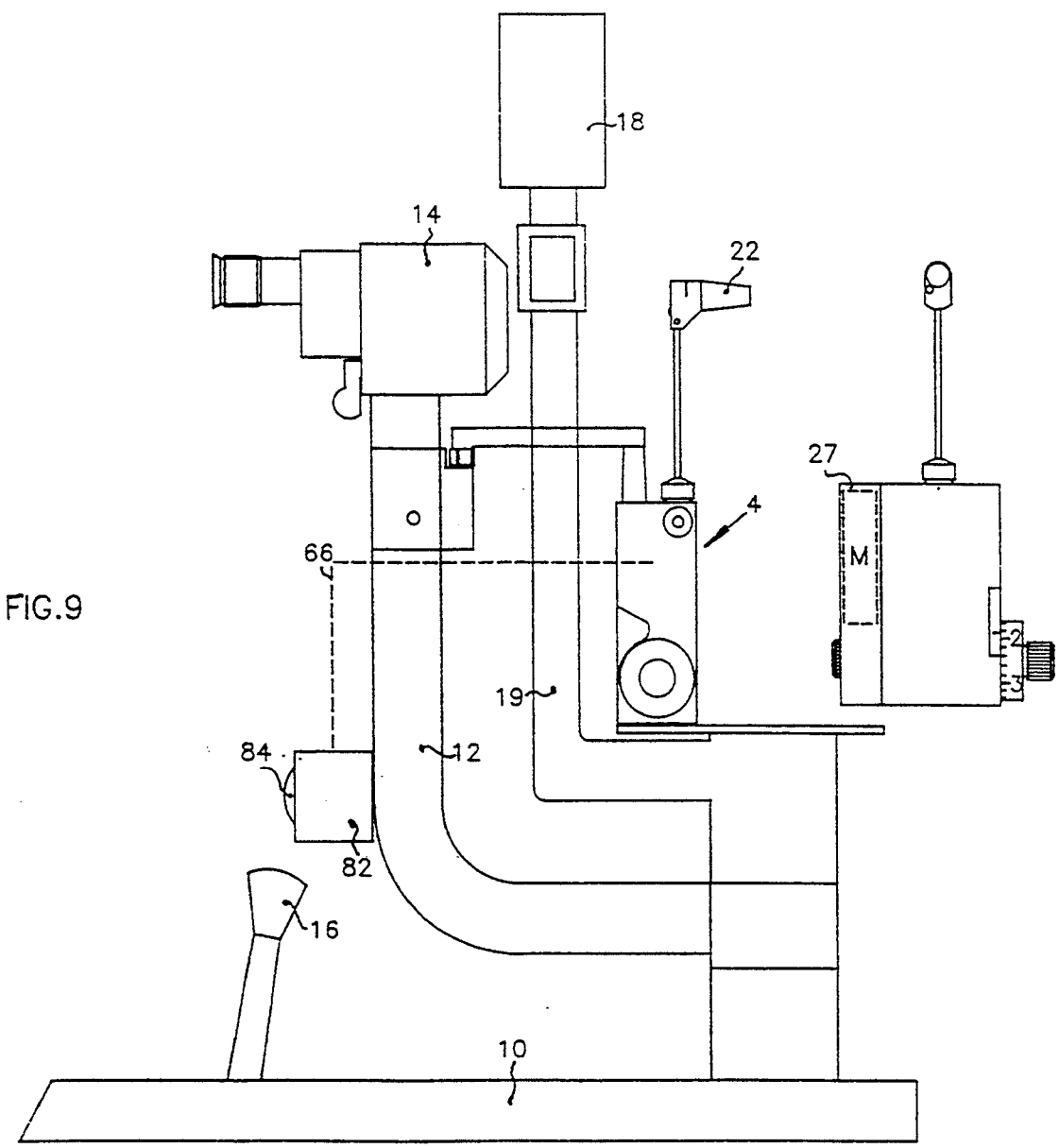

FIG. 9 illustrates an arrangement similar to that of FIG. 8, also including a remote control unit 82 having a manual control member 84 controlling electric motor M within the slave motor housing 27 attached to the tonometer adjusting knob 45 (FIG. 4) via an electrical coupling 66. In this case, however, the manual control member 84 on the remote control unit 82 is the knob of a potentiometer effective to control the rotary displacement of the servo motor M within the slave motor housing 27 according to the amount and direction of rotation of knob 84.

In all the above-described arrangements, the remote control unit of the adjustment accessory is fixed to the arm 12 of the microscope eyepiece 14, as illustrated by bracket 46 in FIG. 1.

Figure 10:
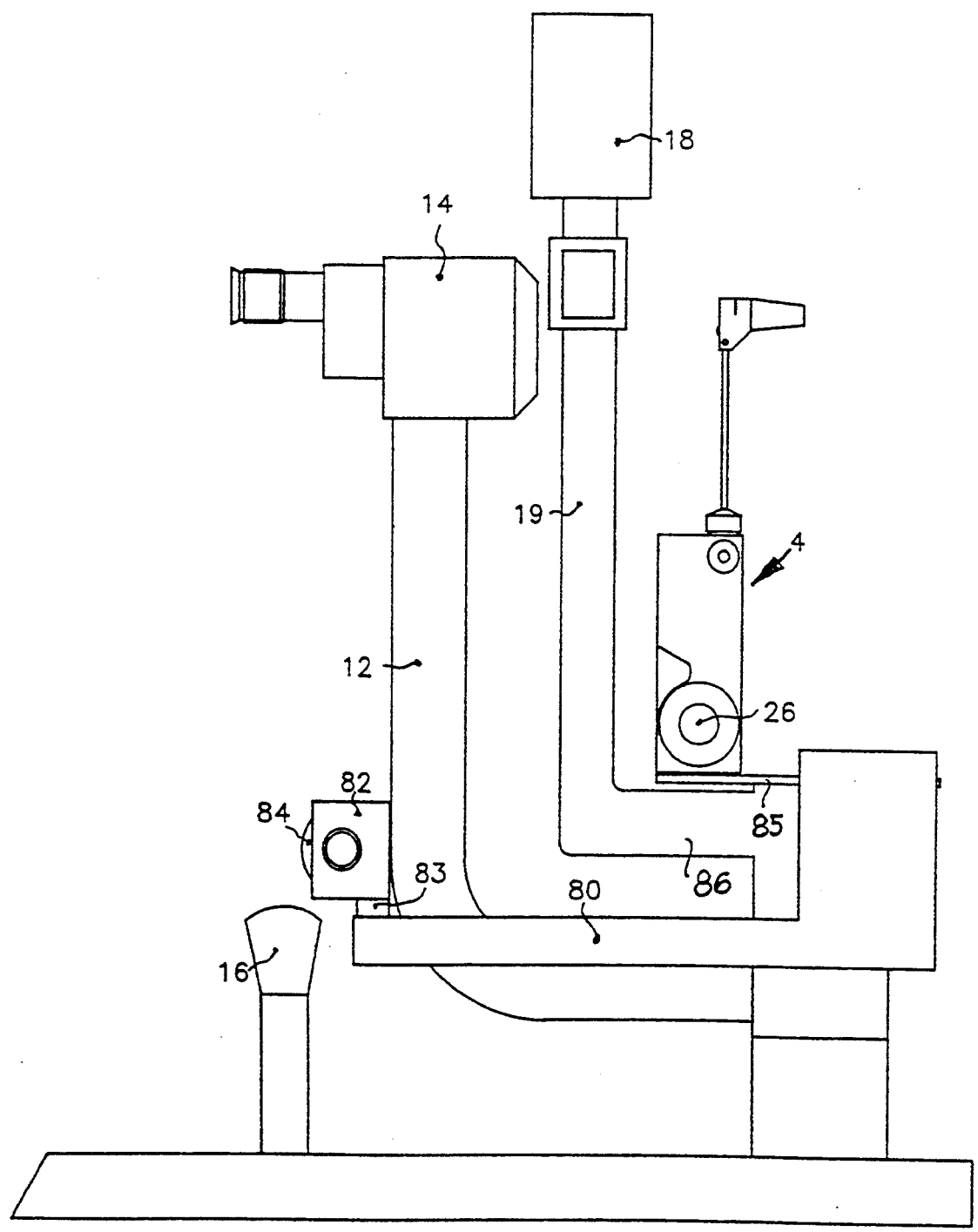
FIG. 10 is a view similar to that of FIG. 1 but illustrating an accessory in accordance with the present invention incorporated in another form of tonometer apparatus and remote control attachment assembly.

FIG. 10 illustrates another arrangement, wherein a mounting arm 80 carries both the tonometer 4 and the remote control unit 82, and mounts both to the lamp arm 19, so that both may be removed at one time. For this purpose, the remote control unit 82 is swivally mounted on a shaft 83 at one end of arm 80, with the manual control member 84 conveniently accessible to the index finger of the examiner's hand while gripping the control lever 16. The opposite end of arm 80 carries a plate 85 to which the tonometer 4 is secured, and which is adapted to rest on a horizontal extension of the lamp arm 19, for supporting thereon both the tonometer 4 and the remote control unit 82. In the normal operating condition, the remote control unit 82 is swivelled to bear against the microscope eyepiece arm 12, as shown in FIG. 10, but when it is desired to remove the remote control unit 82 and the tonometer 4, the remote control unit 82 is swivelled out of engagement with arm 12, permitting removal of the above units as a single assembly.

In all other respects, the arrangement illustrated in FIG. 10 is constructed and operates in the same manner as described above with respect to the other arrangements.

While the invention has been described with respect to several preferred embodiments, it will be appreciated that these are set forth merely for purposes of example, and that many other variations, modifications and applications of the invention may be made.

What is claimed is:

1. An accessory for use with an eye examination apparatus comprising an eyepiece carried at one side, constituting the forward side, of the apparatus to enable an examiner to view a subject's eye located at the opposite side, constituting the rear side, of the apparatus rearwardly of the eyepiece; a control lever for controlling the position of the eyepiece; and a tonometer unit located rearwardly of the eyepiece and including a housing, a contact element to contact the cornea of the subject's eye, and adjusting means for varying the pressure applied by the contact element against the subject's eye;

said accessory comprising: a remote control unit having a manual control member; attaching means for attaching said remote control unit to the apparatus; and a coupling between said manual control member and said adjusting means of said tonometer unit, said manual control member of the remote control unit being sufficiently close to said control lever of the apparatus for controlling the position of the eyepiece such as to permit the operation of both said control lever and said manual control member by the same one hand of the examiner while the examiner views the subject's eye via said eyepiece without lifting said one hand from the control lever or the examiner's eyes from said eyepiece.

2. The accessory according to claim 1, wherein said coupling is a mechanical coupling.

3. The accessory according to claim 2, wherein said mechanical coupling includes a flexible cable having an internally ribbed socket at each of its opposite ends for receiving externally ribbed shafts on said remote control unit and tonometer unit, respectively.

4. The accessory according to claim 3, wherein said mechanical coupling further includes an electrical motor in said remote control unit coupled by said flexible cable to said tonometer unit.

5. The accessory according to claim 4, wherein said manual control member in said remote control unit is a rocker switch.

6. The accessory according to claim 1, wherein said coupling is an electrical coupling.

7. The accessory according to claim 6, wherein said manual control member in said remote control unit is a rocker switch, and said electrical coupling includes an electrical motor attached to said tonometer unit controlled by said rocker switch.

8. The accessory according to claim 6, wherein said manual control member in said remote control unit is a potentiometer, and said electrical coupling includes an electric servo motor attached to said tonometer unit.

9. The accessory according to claim 1, wherein said eyepiece in the eye examination apparatus is carried by an arm adjustably mounted to a base under the control of said control lever, and said attaching means attaches said remote control unit to said arm.

10. The accessory according to claim 1, wherein said remote control unit is carried at one end of an arm, the opposite end of said arm carrying said tonometer unit, to enable quick dismantling of both units.

11. The accessory according to claim 1, wherein said remote control unit further includes a digital display for displaying the adjustments made by moving said manual control member.

12. An eye examination apparatus, comprising:
an eyepiece carried at one side, constituting the forward side, of the apparatus to enable an examiner to view a subject's eye located at the opposite side, constituting the rear side, of the apparatus rearwardly of the eyepiece;
a control lever for controlling the position of the eyepiece;
a tonometer unit located rearwardly of the eyepiece and including a housing, a contact element to contact the cornea of the subject's eye, and adjusting means for varying the pressure applied by the contact element against the subject's eye;
a remote control unit having a manual control member; attaching means for attaching said remote control unit to the apparatus;
and a coupling between said manual control member and said adjusting means of said tonometer unit, said manual control member of the remote control unit being sufficiently close to said control lever of the apparatus for controlling the position of the eyepiece such as to permit the operation of both said control lever and said manual control member by the same one hand of the examiner while the examiner views the subject's eye via said eyepiece without lifting said one hand from the control lever or the examiner's eyes from said eyepiece.

13. The apparatus according to claim 12, wherein said coupling includes a flexible cable having an internally ribbed socket at each of its opposite ends for receiving externally ribbed shafts on said remote control unit and tonometer unit, respectively.

14. The apparatus according to claim 13, wherein said coupling further includes an electrical motor in said remote control unit coupled by said flexible cable to said tonometer unit.

15. The apparatus according to claim 12, wherein said coupling is an electrical coupling.

16. The apparatus according to claim 15, wherein said manual control member in said remote control unit is a rocker switch, and said electrical coupling includes an electrical motor attached to said tonometer unit controlled by said rocker switch.

17. The apparatus according to claim 15, wherein said manual control member in said remote control unit is a potentiometer, and said electrical coupling includes an electric servo motor attached to said tonometer unit.

18. The apparatus according to claim 12, wherein said eyepiece in the eye examination apparatus is carried by an arm adjustably mounted to a base under the control of said control lever, and said attaching means attaches said remote control unit to said arm.

19. The apparatus according to claim 12, wherein said remote control unit is carried at one end of an arm, the opposite end of said arm carrying said tonometer unit, to enable quick dismantling of both units.

20. The apparatus according to claim 12, wherein said remote control unit further includes a digital display for displaying the adjustments made by moving said manual control member.

* * * * *